US008375947B2

(12) United States Patent
Alston et al.

(10) Patent No.: US 8,375,947 B2
(45) Date of Patent: Feb. 19, 2013

(54) INTRODUCING AEROSOL INTO A VENTILATOR

(75) Inventors: William W. Alston, San Jose, CA (US); Sarvajna K. Dwivedi, Redwood City, CA (US); Guy V. Tucker, Berkeley, CA (US)

(73) Assignee: Novartis AG, Basel (CH)

( * ) Notice: Subject to any disclaimer, the term of this patent is extended or adjusted under 35 U.S.C. 154(b) by 308 days.

(21) Appl. No.: 10/991,092

(22) Filed: Nov. 17, 2004

(65) Prior Publication Data

US 2005/0139211 A1    Jun. 30, 2005

Related U.S. Application Data

(60) Provisional application No. 60/523,011, filed on Nov. 17, 2003.

(51) Int. Cl.
*A61M 11/00* (2006.01)
(52) U.S. Cl. ............................. 128/205.24; 128/203.12
(58) Field of Classification Search ............ 128/200.14, 128/203.12, 204.18, 913, 203.15
See application file for complete search history.

(56) References Cited

U.S. PATENT DOCUMENTS

| | | | |
|---|---|---|---|
| 4,529,003 A * | 7/1985 | Iannuzzelli et al. ....... | 137/493.8 |
| 4,838,259 A * | 6/1989 | Gluck et al. ............ | 128/204.21 |
| 5,007,420 A * | 4/1991 | Bird ...................... | 128/200.14 |
| 5,116,088 A * | 5/1992 | Bird ...................... | 285/319 |
| 5,666,946 A * | 9/1997 | Langenback ........... | 128/200.16 |
| 6,565,885 B1 | 5/2003 | Tarara et al. | |
| 6,615,824 B2 | 9/2003 | Power | |
| 6,630,169 B1 | 10/2003 | Bot et al. | |
| 6,946,117 B1 | 9/2005 | Schutt et al. | |
| 2002/0002975 A1* | 1/2002 | Power ................... | 128/203.12 |
| 2003/0196660 A1* | 10/2003 | Haveri .................. | 128/203.12 |
| 2004/0234610 A1* | 11/2004 | Hall et al. ............... | 424/489 |
| 2005/0186146 A1 | 8/2005 | Gong et al. | |
| 2005/0211245 A1* | 9/2005 | Smaldone et al. ....... | 128/204.18 |
| 2005/0217666 A1 | 10/2005 | Fink et al. | |
| 2005/0229928 A1 | 10/2005 | Ivri et al. | |
| 2005/0229929 A1* | 10/2005 | Ivri ....................... | 128/203.12 |
| 2005/0271660 A1* | 12/2005 | Wang .................... | 424/144.1 |
| 2006/0283447 A1* | 12/2006 | Dhuper et al. .......... | 128/203.12 |

FOREIGN PATENT DOCUMENTS

WO    2004/071368    8/2004

* cited by examiner

*Primary Examiner* — Steven Douglas
(74) *Attorney, Agent, or Firm* — Janah & Associates, P.C.

(57) ABSTRACT

An aerosol introducer is provided for introducing an aerosolized pharmaceutical formulation into a ventilator circuit. The ventilator circuit comprises an endotracheal tube, an inhalation line extending from a ventilator, and an exhalation line extending from the ventilator. The aerosol introducer comprises a first end connectable to the inhalation line and the exhalation line; a second end connectable to the endotracheal tube; a first channel extending from the first end to the second end; a second channel extending from the first end to the second end; an inlet in the first channel, the inlet being adapted to receive an aerosolized pharmaceutical formulation; and a valving mechanism comprising one or more valves that reduce the loss of aerosolized pharmaceutical formulation to the exhalation line.

13 Claims, 11 Drawing Sheets

Figure 1

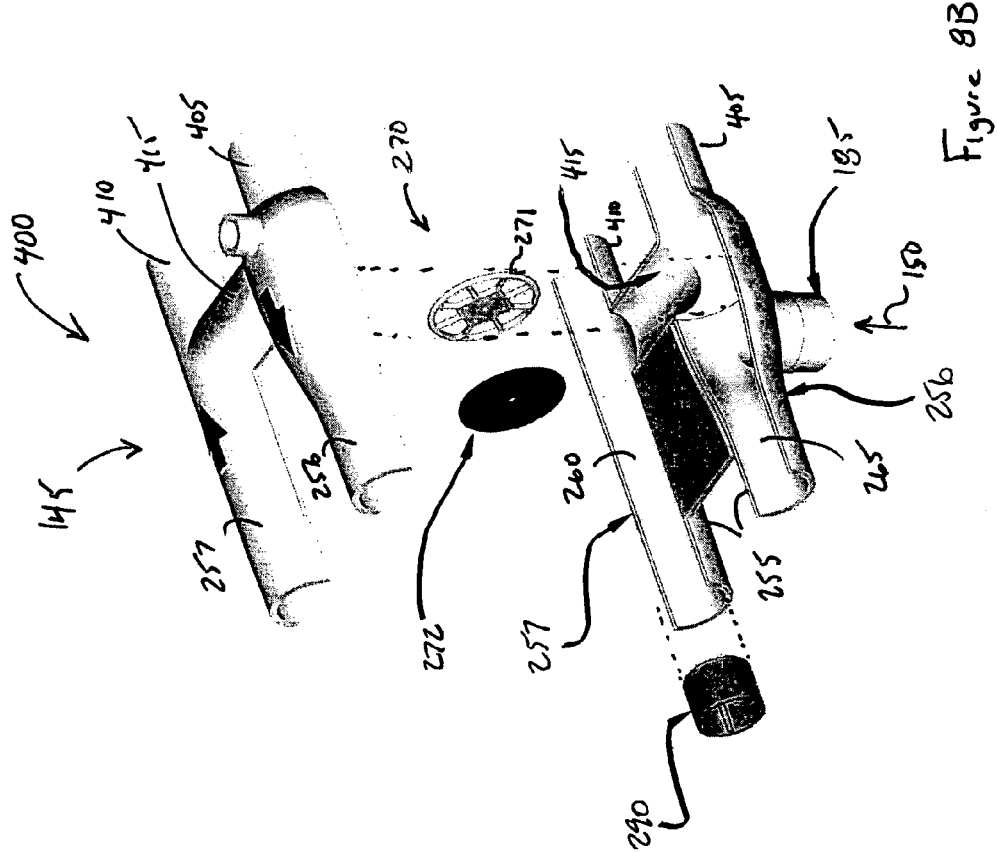

INTRODUCING AEROSOL INTO A VENTILATOR

This application claims the benefit U.S. Provisional Patent Application Ser. No. 60/523,011 filed on Nov. 17, 2003, which is incorporated herein by reference in its entirety.

BACKGROUND

The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before they can be effectively absorbed by the body. Inhaleable drug delivery, where an aerosolized pharmaceutical formulation is orally or nasally inhaled by a patient to deliver the formulation to the patient's respiratory tract, has proven to be a particularly effective and/or desirable alternative. In one inhalation technique, an aerosolized pharmaceutical formulation provides local therapeutic treatment and/or prophylaxis to a portion of the respiratory tract, such as the lungs, to treat respiratory diseases such as asthma and emphysema and/or to treat local lung infections, such as fungal infections and cystic fibrosis. In another inhalation technique, a pharmaceutical formulation is delivered deep within a patient's lungs where it may be absorbed into the blood stream for systemic delivery of the pharmaceutical throughout the body. Many types of aerosolization devices exist including devices comprising a pharmaceutical formulation stored in or with a propellant, devices that aerosolize a dry powder, devices which use a compressed gas or other mechanism to aerosolize a liquid pharmaceutical formulation, and similar devices.

One conventional type of aerosolization device is commonly referred to as a nebulizer. A nebulizer comprises a container having a reservoir which contains a liquid pharmaceutical formulation. The liquid pharmaceutical formulation generally comprises an active agent that is either in solution or suspended within a liquid medium. Energy is introduced into the reservoir to aerosolize the liquid pharmaceutical formulation so that it may be delivered to the lungs of a user. In one type of nebulizer, generally referred to as a jet nebulizer, compressed gas is forced through an orifice in the container. The compressed air forces liquid to be withdrawn through a nozzle, and the withdrawn liquid mixes with the flowing gas to form aerosol droplets. A cloud of the droplets is then administered to the user's respiratory tract. In another type of nebulizer, generally referred to as a vibrating mesh nebulizer, energy such as ultrasonic waves are generated to vibrate a mesh. This vibration of the mesh aerosolizes the liquid pharmaceutical formulation to create an aerosol cloud that is administered to the user's lungs. Nebulizers are sometimes cumbersome to use. However, nebulizers are particularly useful in delivering an aerosolized pharmaceutical formulation to a hospitalized or non-ambulatory patient; in delivering large doses of aerosolized active agent; and/or when delivering an aerosolized pharmaceutical formulation to a child or other patient unable to receive a dry powder or propellant based pharmaceutical formulation.

Nebulizers are particularly useful for delivering an aerosolized pharmaceutical formulation to the respiratory tract of a patient who is breathing under the assistance of a ventilator. However, there are problems associated with the introduction of the aerosolized pharmaceutical formulation into the ventilator circuit. For example, by introducing the aerosolized pharmaceutical formulation into the inspiratory line of the ventilator, significant residence volume exists between the point of introduction and the patient's lungs. Accordingly, large volumes of aerosolized pharmaceutical formulation are needed and much of the volume is lost to the exhalation line. This problem is exacerbated when the nebulizer is used in conjunction with ventilators having continual bias flows. In addition, the large residence volume in the ventilator line may dilute the aerosolized pharmaceutical formulation to an extent where the amount delivered to the patient is difficult to reproduce consistently.

Therefore, it is desirable to provide a way to introduce an aerosolized pharmaceutical formulation to a ventilated patient in an effective and consistent manner. It is further desirable to introduce the aerosolized pharmaceutical formulation in a manner that reduces the loss of active agent. It is further desirable to introduce the aerosolized pharmaceutical formulation in a manner that is applicable over a broad range of ventilators and a broad range of practices.

SUMMARY

The present invention satisfies these needs. In one aspect of the invention, a dual channel aerosol introducer is provided.

In another aspect of the invention, an aerosol introducer is provided for introducing an aerosolized pharmaceutical formulation into a ventilator circuit, the ventilator circuit comprising an endotracheal tube, an inhalation line extending from a ventilator, and an exhalation line extending from the ventilator. The aerosol introducer comprises a first end connectable to the inhalation line and the exhalation line; a second end connectable to the endotracheal tube; a first channel extending from the first end to the second end; a second channel extending from the first end to the second end; an inlet in the first channel, the inlet being adapted to receive an aerosolized pharmaceutical formulation; and a valving mechanism comprising one or more valves that reduce the loss of aerosolized pharmaceutical formulation to the exhalation line.

In another aspect of the invention, an aerosol introducer is provided for delivering an aerosolized pharmaceutical formulation to a patient. The aerosol introducer comprises a first end; a second end comprising a opening for delivering aerosol to a user's mouth or nose; a first channel extending from the first end to the second end; a second channel extending from the first end to the second end; an inlet in the first channel, the inlet being adapted to receive an aerosolized pharmaceutical formulation; and a valve in the first or second channel.

In another aspect of the invention, a method of introducing an aerosolized pharmaceutical formulation into a ventilator circuit comprises providing an aerosol introducer comprising a first end, a second end, a first channel extending from the first end to the second end, a second channel extending from the first end to the second end, an inlet in the first channel, and a valve within the first channel and/or the second channel, connecting the first end to an inhalation line and an exhalation line extending from a ventilator; connecting the second end to an endotracheal tube; and receiving the aerosolized pharmaceutical formulation through the inlet and into the first channel.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

FIG. 1 is a schematic sectional view of an aerosolized pharmaceutical formulation delivery system according to the invention;

FIGS. 8A-8C are schematic views of another version of an aerosol introducer, FIG. 8A being a perspective view, FIG. 8B being an exploded view, and FIG. 8C showing a version with a flexible portion.

DESCRIPTION

Figure 2A:
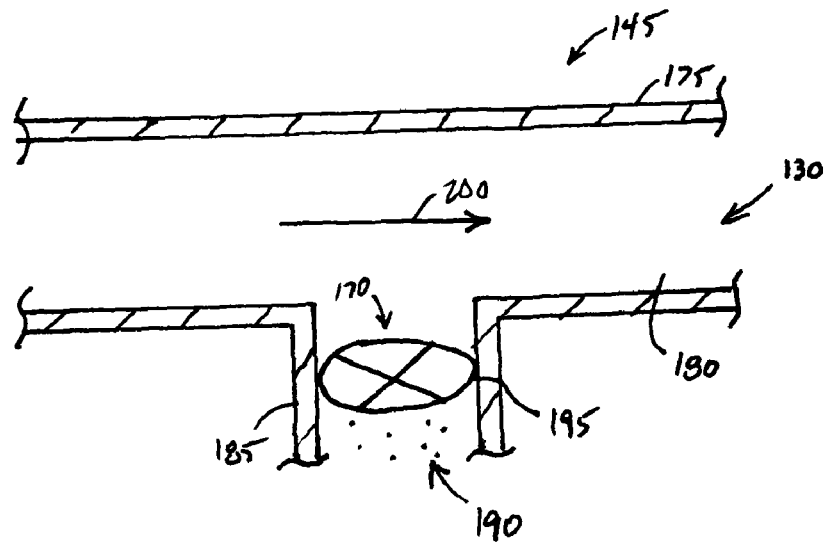
FIGS. 2A and 2B are schematic sectional side views of a version of an aerosol introducer according to the invention.

The present invention relates to an aerosolizable pharmaceutical formulation. In particular, the invention relates to an aerosolizable liquid pharmaceutical formulation for administration to a patient on a ventilator. Although the invention is illustrated in the context of a liquid pharmaceutical formulation for a nebulizer, the present invention can be used in other processes and should not be limited to the examples provided herein.

Figure 1:
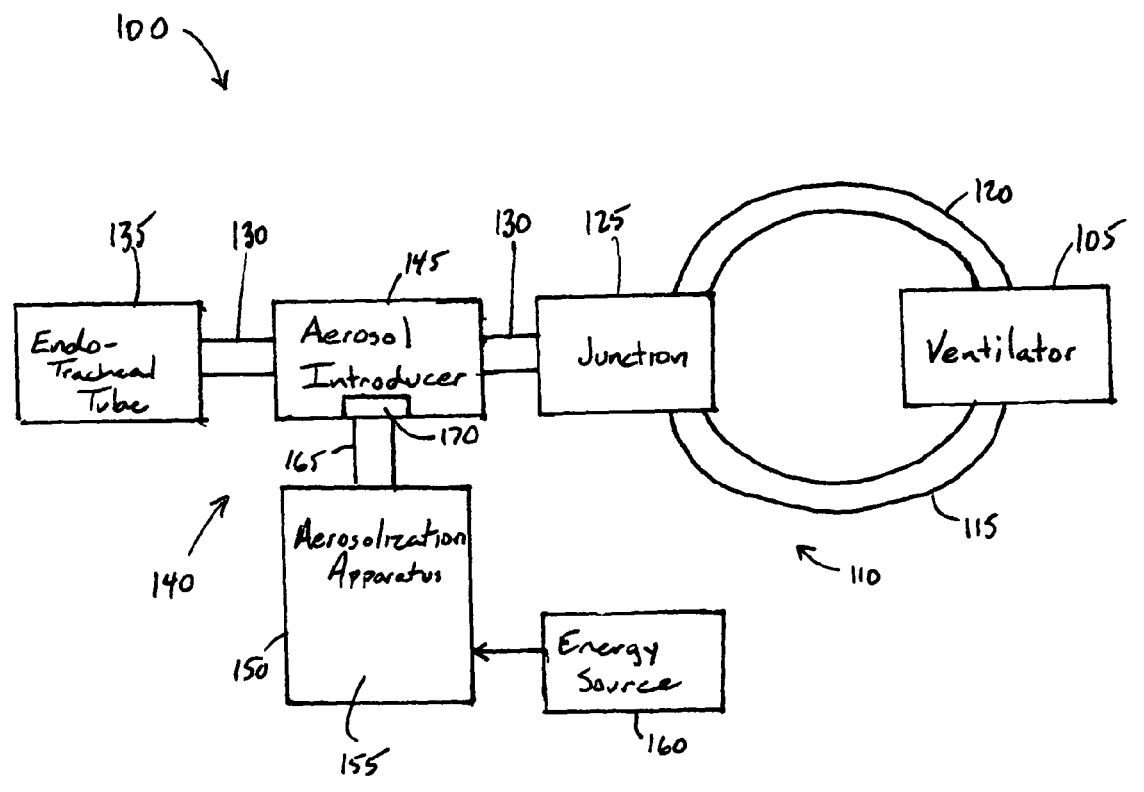

An aerosolized pharmaceutical formulation delivery system 100 according to the invention is shown in FIG. 1. The aerosolized pharmaceutical formulation delivery system 100 delivers an aerosolized pharmaceutical formulation to a portion of a user's respiratory tract, such as to the user's lungs. The aerosolized pharmaceutical formulation delivery system 100 is particularly useful in delivering the aerosolized pharmaceutical formulation to a patient whose breathing is being assisted by a ventilator 105 but may also be configured to be used to deliver a pharmaceutical formulation to a non-ventilated patient, as discussed below. The ventilator circuit 110 is shown diagrammatically in FIG. 1. Extending from the ventilator 105 is an inhalation line 115 and an exhalation line 120. The inhalation line 115 and the exhalation line 120 each are composed of tubing having an airflow lumen extending therethrough. The inhalation line 115 and the exhalation line 120 meet at a junction 125 remote from the ventilator 105. At the junction 125 the lumen of the inhalation line 115 is in communication with the lumen from the exhalation line 120, and both of the aforementioned lumen are in communication with a patient line 130. The patient line 130 comprises a lumen that extends to the lumen of an endotracheal tube 135 which is inserted into the mouth of a patient. The endotracheal tube 135 has an opposite end that extends into or near the lungs of the user. Accordingly, in use, oxygenated air is introduced into the inhalation line 115 by the ventilator 105. The oxygenated air passes through the lumen of the inhalation line 115, into the patient line 130, through the lumen of the endotracheal tube 135, and into the lungs of the patient. The patient then exhales, either naturally or by applying negative pressure from the ventilator, and the exhaled air passes through the endotracheal tube 135, through the patient line 130, and through the exhalation line 120 to the ventilator 105. The cycle is continuously repeated to assist the patient's breathing or to entirely control the breathing of the patient.

The aerosolized pharmaceutical formulation delivery system 100 further comprises an aerosol introduction mechanism 140. The aerosol introduction mechanism 140 comprises an aerosol introducer 145 that introduces aerosolized pharmaceutical formulation into the ventilator circuit 110 at a position between the junction 125 and the lungs of the patient. For example, the aerosol introducer may introduce the aerosolized pharmaceutical formulation into the patient line 130, as shown in FIG. 1, or may introduce the aerosolized pharmaceutical formulation within or near the endotracheal tube 135. The aerosol that is introduced by the aerosol introducer 145 is generated by an aerosolization apparatus 150 which comprises a reservoir for containing a pharmaceutical formulation. Aerosolization energy is supplied to the aerosolization device by an energy source 160 to generate the aerosolized pharmaceutical formulation. The aerosolized pharmaceutical formulation passes through a passage 165 to the aerosol introducer 145 where it may be introduced into the ventilator circuit 110. The aerosolization apparatus 150 may be, for example, a jet nebulizer where the energy source is compressed air, a vibrating mesh nebulizer where the energy source is a wave of energy, a metered does inhaler where the energy source is a propellant that boils under ambient conditions, or a dry powder inhaler where the energy source is compressed or flowing air or is a vibrating membrane or the like.

An example of an aerosol introducer 145 for introducing the aerosolized pharmaceutical formulation at a position between the junction 125 and the lungs of the patient is described in Gerald Smaldone et al's PCT Patent Application No. PCT/US2003/014708 entitled "Methods, Devices and Formulations for Targeted Endobronchial Therapy", filed on May 7, 2003 and published as WO 2004/071368; in Gerald Smaldone et al's U.S. patent application Ser. No. 10/430,765, filed on May 6, 2003; in Gerald Smaldone et al's U.S. patent application Ser. No. 10/430,658, filed on May 6, 2003; and in U.S. Provisional Patent Applications 60/378,475; 60/380,783; 60/420,429; 60/439,894; and 60/442,785, all of which are incorporated herein by reference in their entireties.

The introduction of the aerosolized pharmaceutical formulation at a position between the junction 125 and the lungs of the patient is advantageous in many respects over the prior art systems where the aerosol is introduced into the inhalation line 115 or within the ventilator 105. For example, by introducing the aerosolized pharmaceutical formulation at a position between the junction 125 and the lungs of the patient, the ventilator circuit volume from the point of introduction to the patient's lungs is substantially reduced. Accordingly, the aerosolized pharmaceutical formulation is more concentrated and is less diffused throughout the ventilator circuit 110. In addition, by residing in the inhalation line 115, much of the prior art aerosolized pharmaceutical formulation is drawn into the exhalation line 120, further limiting the efficiency of the administration. Because of this diffusion and this reduced efficiency, the consistency of dosing is difficult to control with the prior art systems. Also, the presence of high quantities of the aerosolized pharmaceutical formulation that are not administered to the lungs of the patient may be undesirable in that much of the aerosol may be introduced into the environment where it may be inhaled by healthcare workers or others.

While the introduction of the pharmaceutical formulation at a position between the junction 125 and the lungs of the patient is advantageous over the state of the art systems, as discussed above, it has been discovered that much of the introduced aerosolized pharmaceutical formulation may still be drawn into the exhalation line 120 prior to be administered to the patient. Therefore, the aerosol introducer 145 according to the invention has been designed to introduced the aerosolized pharmaceutical formulation in an improved manner to increase the efficiency and/or the consistency of the dosing. Accordingly, the aerosol introducer 145 introduces the aerosolized pharmaceutical formulation into the inhalation flow at a position between the junction 125 and the lungs of the patient. In this way, the aerosol introducer 145 serves to reduce the amount of aerosolized pharmaceutical formulation that is drawn into the exhalation line 120 of the ventilator circuit 120.

In one version, the aerosol introducer 145 comprises a valving mechanism 170 to control the introduction of the aerosolized pharmaceutical formulation. For example, the valving mechanism 170 may comprise one or more valves that prevent or reduce the introduction of the aerosolized pharmaceutical formulation into the patient line 130 during the exhalation phase of the ventilator cycle and/or that prevent or reduce aerosolized pharmaceutical formulation present in the patient line 130 from being drawn out of the patient line 130 during the exhalation phase of the ventilator cycle.

Figure 2B:
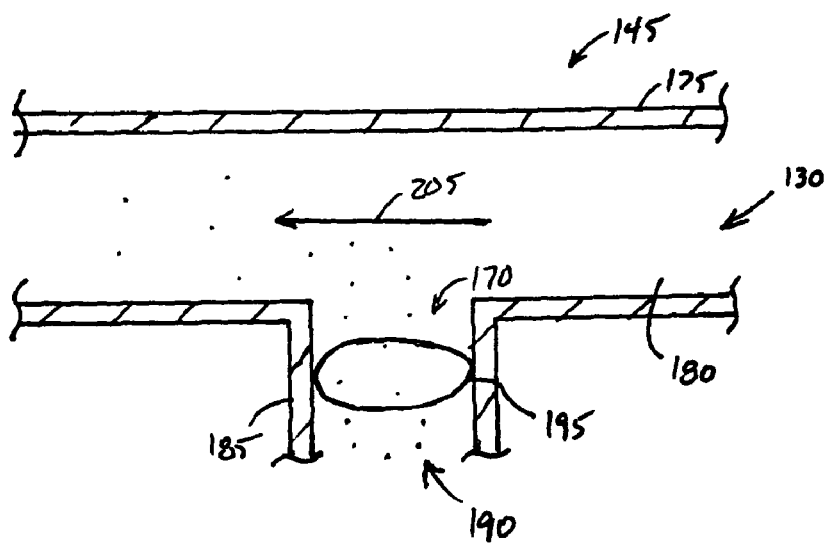

A version of an aerosol introducer 145 which prevents or reduces the introduction of aerosolized pharmaceutical formulation into the exhalation line 120 is shown in FIGS. 2A and 2B. In this version, the aerosol introducer 145 comprises a body 175 that defines a lumen 180 which makes up at least a portion of the patient line 130. The body 175 of the aerosol introducer 145 has an extension portion 185 that is in communication with the aerosolization apparatus 150 and is able to receive aerosolized pharmaceutical formulation 190. Within the extension portion 185 a selectively openable valve 195 is positioned. The valve 195 is in a closed position during exhalation 200, as shown in FIG. 2A, and is then in an open position during inhalation 205, as shown in FIG. 2B.

Figure 3A:
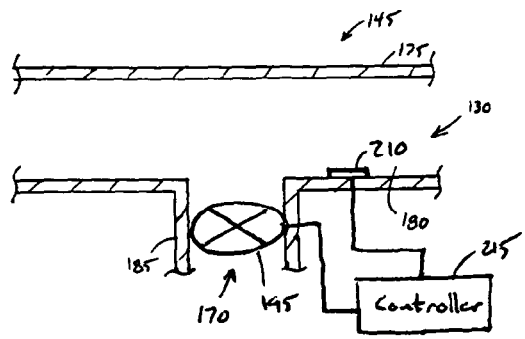
FIGS. 3A through 3C are schematic sectional side views of versions of an aerosol introducer.
Figure 3B:
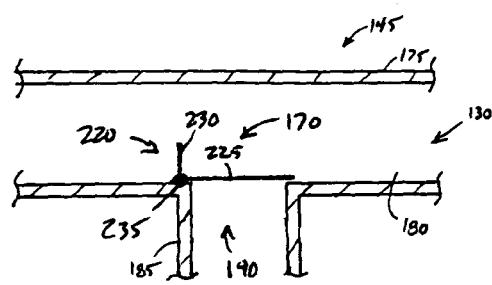
Figure 3C:
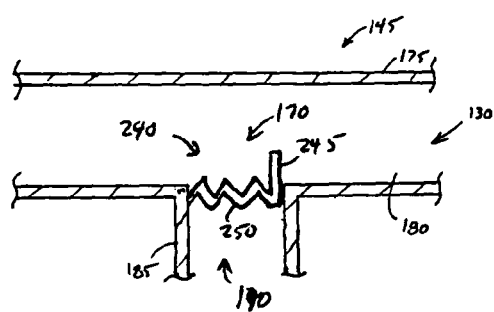

Examples of the aerosol introducer 145 according to the version of FIGS. 2A and 2B are shown in FIGS. 3A through 3C. In the version shown in FIG. 3A, a detector 210, such as a flow sensor, is positioned in the patient line 130 or elsewhere in the system to detect the occurrence of the inhalation phase or the exhalation phase. The detector 210 transmits a signal to a controller 215, such as a microprocessor or ASICs, which then generates a control signal in response to the detector signal to control the operation of the valve 195. Thus, when a signal from the detector 210 is determined to be indicative of an inhalation phase, the controller 215 causes the valve 195 to be in an open state, and when an exhalation phase is detected, the controller 215 causes the valve 195 to be in a closed state. In the versions of FIGS. 3B and 3C, the valve 195 is a mechanical valve that operates in response to the flow of air in the lumen 180. In the version of FIG. 3B, an L-shaped member 220 comprises a covering portion 225 that covers the extension portion 185 in the closed position to prevent the flow of aerosolized pharmaceutical formulation into the lumen 180. During inhalation, the flow of air contacts a protrusion 230 on the L-shaped member 220 which causes the L-shaped member 220 to pivot about a hinge 235 thereby lifting the covering portion at a position between the junction 125 and the lungs of the patient 225 and allowing the aerosolized pharmaceutical formulation to be introduced into the lumen 180. In the version of FIG. 3C, a compressible member 240 comprises a protrusion 245 that is acted on by the flowing air in the lumen 180. During inhalation, the flowing air causes the compressible member 240 to compress, for example by compressing an accordion section 250, thereby opening the extension portion 185, and during exhalation, the air flow cause the compressible member 240 to extend to the position shown in FIG. 3C to close the extension portion 185 and prevent or reduce the flow of aerosolized pharmaceutical formulation into the lumen 180.

Figure 4A:
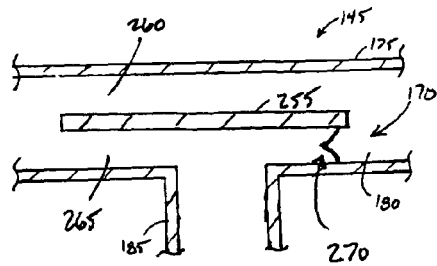
FIGS. 4A through 4D are schematic sectional side views of other versions of an aerosol introducer.

In another version, the lumen 180 of the aerosol introducer 145 is configured to prevent or reduce aerosolized pharmaceutical formulation present in the patient line 130 from being drawn out of the patient line 130 during the exhalation phase of the ventilator cycle. For example, as shown in FIG. 4A, in one version, a wall 255 may be provided in the lumen 180 to divide the lumen into multiple channels, such as a first channel 265 and a second channel 260. The first channel 265 is in communication with the extension portion 185 so as to receive the aerosolized pharmaceutical formulation. In the version of FIG. 4A, a one-way valve 270 is positioned in the first channel 265 so that only inhalation flow may pass through the first channel 265. Accordingly, only when inhalation air is flowing passed the extension portion 185 will aerosolized pharmaceutical formulation be drawn out of the aerosolization apparatus and delivered to the endotracheal tube and the patient. During exhalation, there is no flow through first channel 265, and aerosolized pharmaceutical formulation from the aerosolization apparatus is not withdrawn and excess aerosolized pharmaceutical formulation in the extension portion 185 and in the first channel 265 is not forced into the exhalation line 120.

Figure 4B:
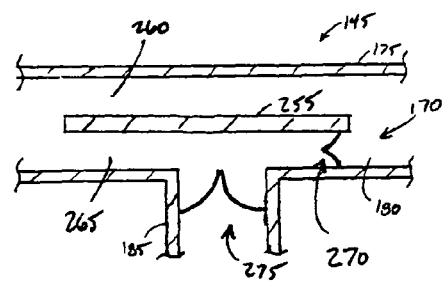
Figure 4C:
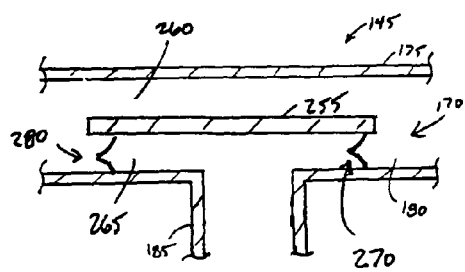
Figure 4D:
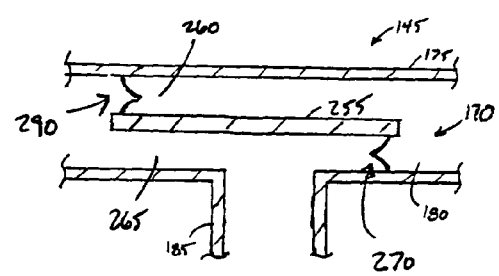

Other versions of an aerosol introducer 145 having multiple channels are shown in FIGS. 4B through 4D. In the version of FIG. 4B, a one-way valve 275 is positioned within the extension portion 185. In one version, the one-way valve 275 opens when air is flowing in the first channel 265. Since only inhalation flow is permitted in the first channel 265, as discussed above, the one-way valve 275 is only open during the inhalation phase. In the version of FIG. 4C, a second one-way valve 280 is placed in the first channel 265 on the opposite side of the extension portion 185 from the first one-way valve 270. This valve prevents aerosolized pharmaceutical formulation within the first channel 265 from being driven back into the aerosolization apparatus and prevents any aerosolized pharmaceutical formulation in the first channel 265 from being drawn into the exhalation air flow in the first channel 260. In the version of FIG. 4D, an oppositely directed one-way valve 290 is positioned in the second channel 260. In this version, only exhalation flow passes through the second channel 260. Accordingly, all of the inhalation flow passes through the first channel 265. In other version, the aerosol introducer includes a combination of any of the features shown in FIGS. 4A through 4D. Also, the cross-sectional dimensions of the channels may be adjusted and/or may vary relative to one another and/or may vary relative to the other dimensions within the patient line 130 to allow for desired flow characteristics in the system.

The orientation of the extension portion 185 and the first channel 265 may be configured to improve the delivery efficiency of the aerosolized pharmaceutical formulation delivery system 100. For example, in one version the extension portion 185 may be oriented at a right angle with the first channel 265, as shown in FIGS. 4A through 4D. In another version, the extension portion 185 may be oriented at an acute angle relative to the direction of inhalation flow from the inhalation line 115. In this version, the flow of aerosolized pharmaceutical formulation from the aerosolization apparatus 150 will be less likely to impact the wall 255 or other divider in the introducer 145. In particular versions, the acute angle is from about 10 degrees to about 89 degrees, more preferably from about 20 degrees to about 80 degrees, and most preferably from about 30 degrees to about 45 degrees. This version is particularly useful when the aerosolization apparatus 150 comprises a jet nebulizer. In another version, the extension portion 185 may be oriented at an obtuse angle relative to the direction of inhalation flow from the inhalation line 115. In this version, the flow of aerosolized pharmaceutical formulation from the aerosolization apparatus 150 will be more likely to mix with the oncoming inhalation flow. In particular versions, the obtuse angle is from about 91 degrees to about 179 degrees, more preferably from about 10 degrees to about 160 degrees, and most preferably from about 135 degrees to about 150 degrees.

Figure 5A:
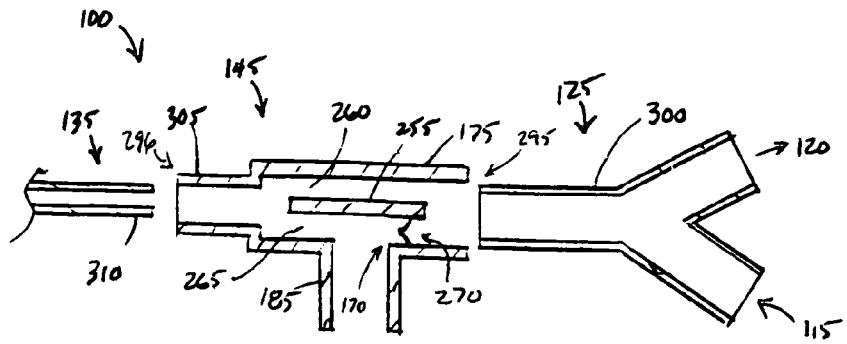
FIGS. 5A through 5C are schematic sectional side views of other versions of an aerosol introducer.
Figure 5B:
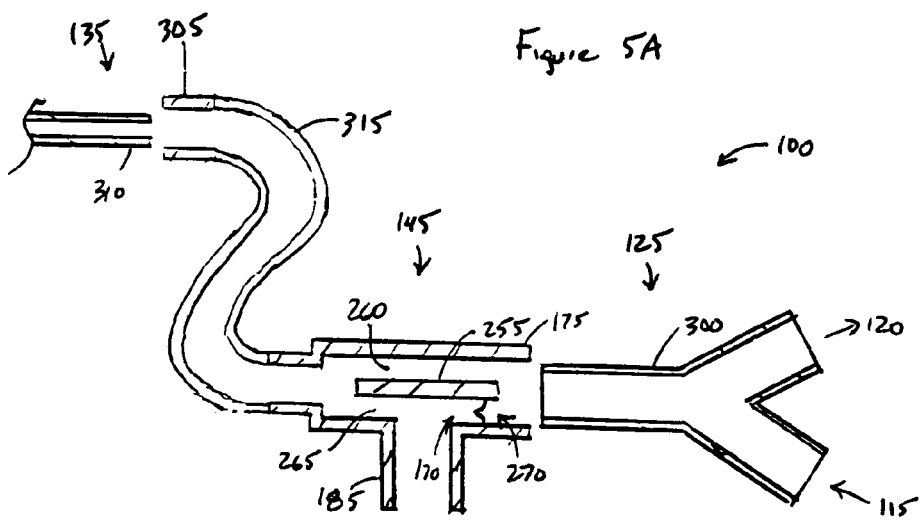
Figure 5C:
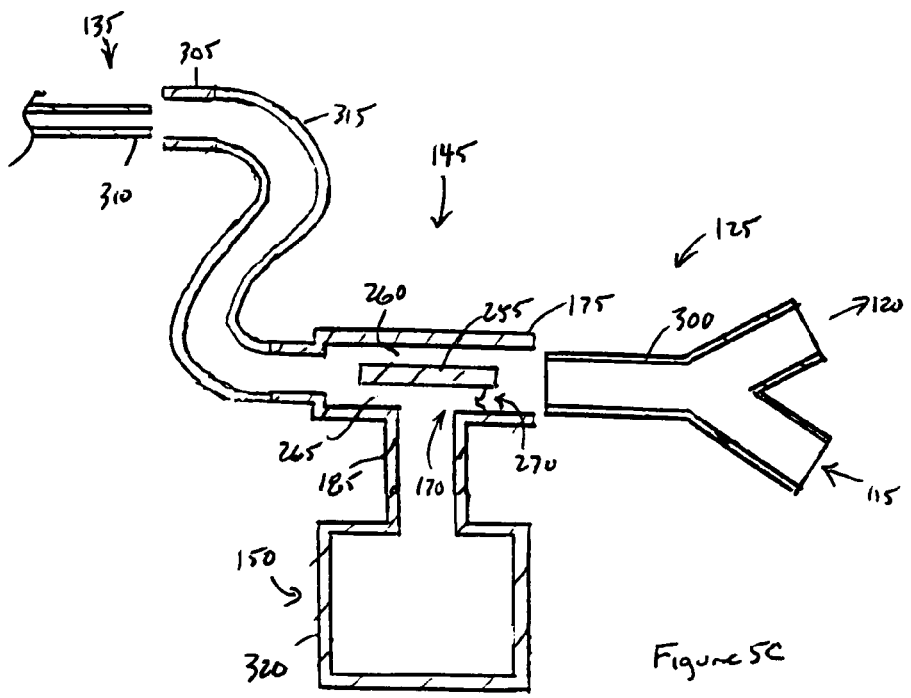

The aerosol introducer 145 may be configured for simple installation into a convention ventilator circuit 110. For example, as shown in FIG. 5A, the aerosol introducer 145 may comprise an adapter having a first end 295 that is adapted to be connected to a conventional Y-piece serving as the junction 125. The aerosol introducer 145 of this version also comprises a second end 296 that is adapted to be connected to an end 310 of a conventional endotracheal tube 135. The extension portion 185 in this version is adapted to be connected to an output end of an aerosolization apparatus 150. FIG. 5B shows another version of an aerosol introducer 154. This version is similar to the version of FIG. 5A and further comprises a flexible portion 315 which allows the aerosol introducer to be placed a distance from the mouth of the patient. FIG. 5C shows another version similar to the versions of FIGS. 5A and 5B, but with the aerosolization apparatus 150 and the aerosol introducer being integrated and/or being formed of a single piece. In the version of FIGS. 5A, 5B, and 5C, the aerosol introducer 145 is in accordance with the version described in FIG. 4A. However, any of the aforementioned versions may be substituted for the versions shown. When using the versions of FIGS. 5A through 5C, a healthcare worker disconnects the Y-piece 300 from the endotracheal tube 135 and inserts the aerosol introducer 145 between the two parts.

Figure 6A:
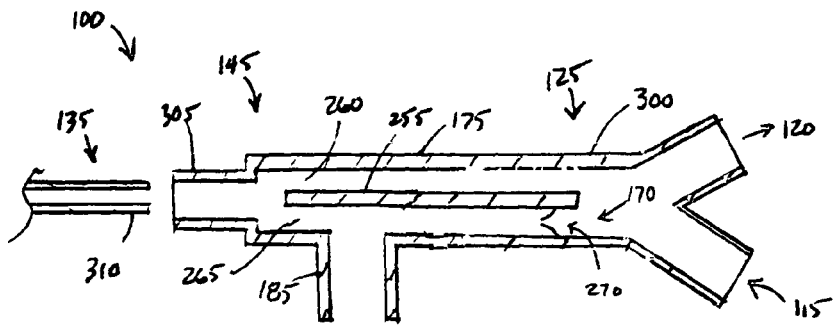
FIGS. 6A through 6C are schematic sectional side views of other versions of an aerosol introducer.
Figure 6B:
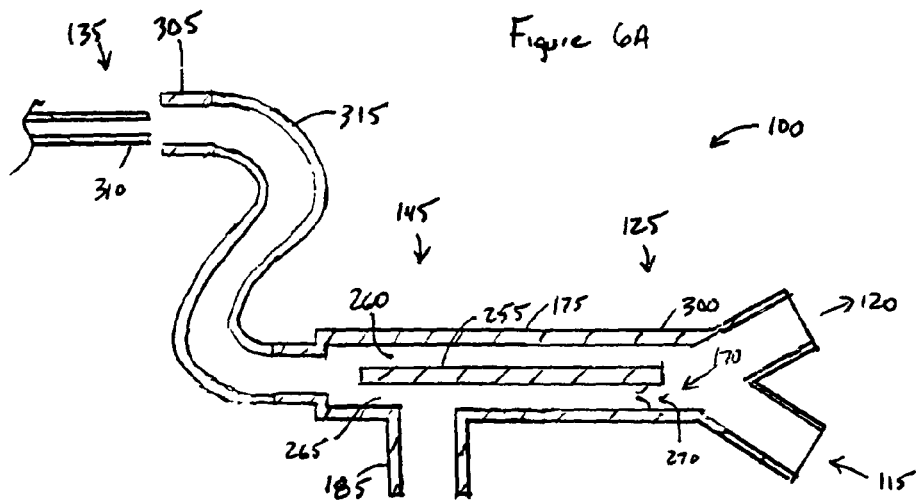
Figure 6C:
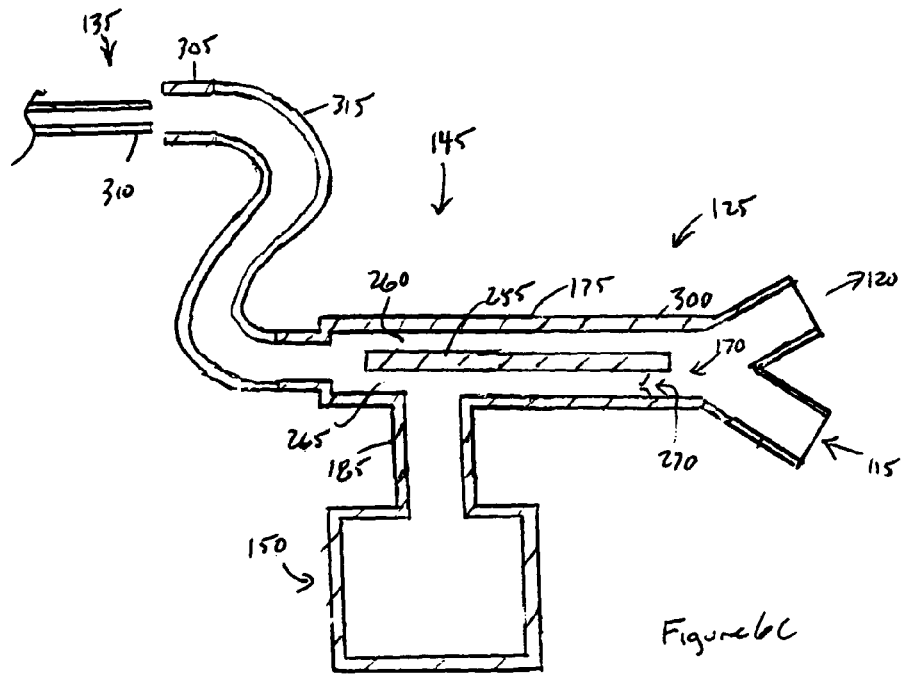

Another version of an aerosol introducer 145 is shown in FIGS. 6A through 6C. These versions are similar to the versions of FIGS. 5A through 5C, respectively, but with the Y-piece formed as an integral and/or single piece with the aerosol introducer 145. When using the versions of FIGS. 6A through 6C, a healthcare worker disconnects a Y-piece 300 from the endotracheal tube 135 and from the inhalation line 115 and the exhalation line 120. One of the aerosol introducers 145 of FIGS. 6A through 6C in then connected to the endotracheal tube 135 and to the inhalation line 115 and the exhalation line 120.

Figure 7:
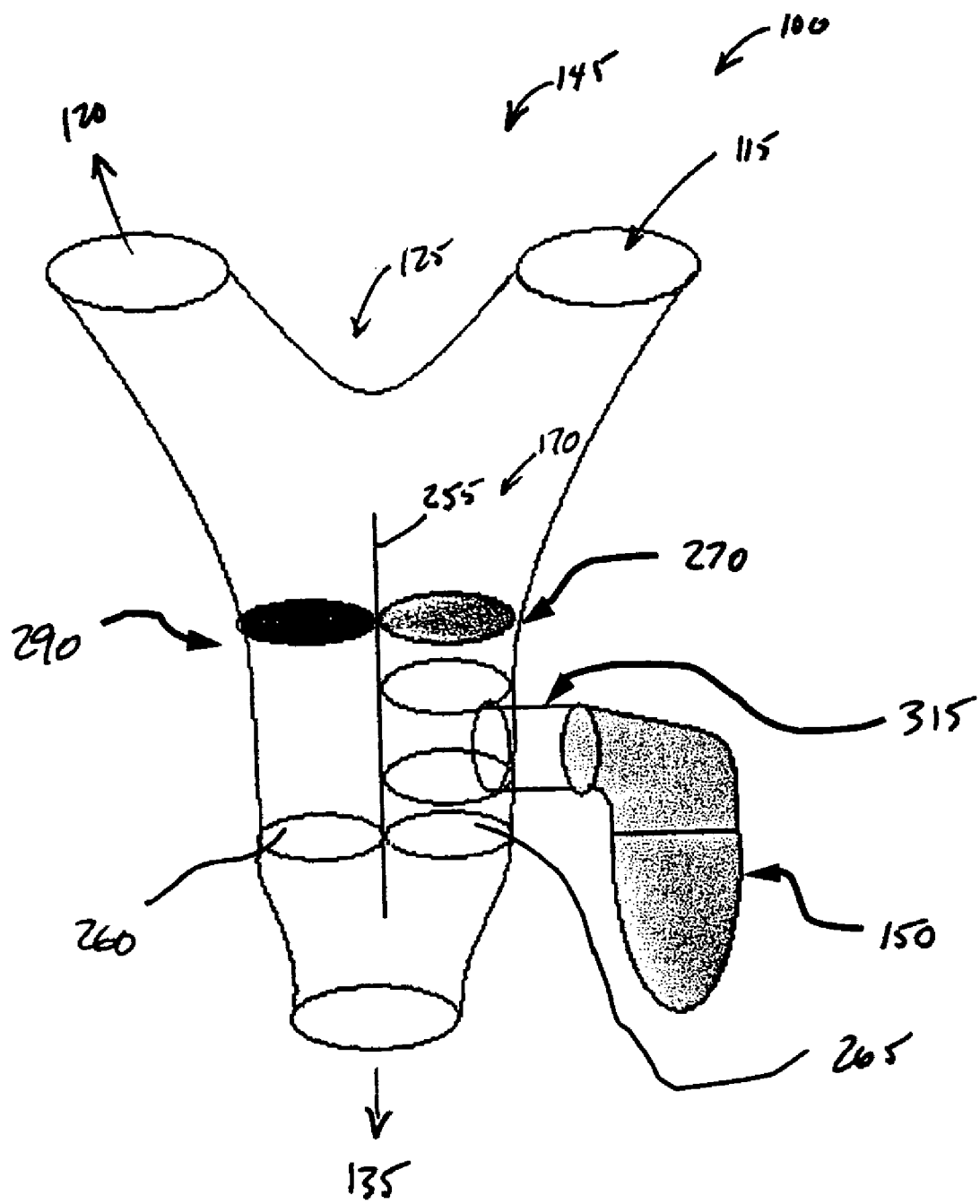
FIG. 7 is a schematic sectional side view of another version of an aerosol introducer.

A specific version of an aerosol introducer 145 that is integrated into a Y-piece junction 125 is shown in FIG. 7. This version is similar to the version of FIG. 4D. In this version, the aerosol introducer 145 further comprises a swivel joint 315 which allows the orientation of the aerosolization apparatus 150 to be adjusted during use. A wall 255 is provided to separate the first channel 265 and the second channel 260. Optionally, an HME filter may be provided in the second channel 260, for example at a position just before the one-way valve 290.

Figure 8A:
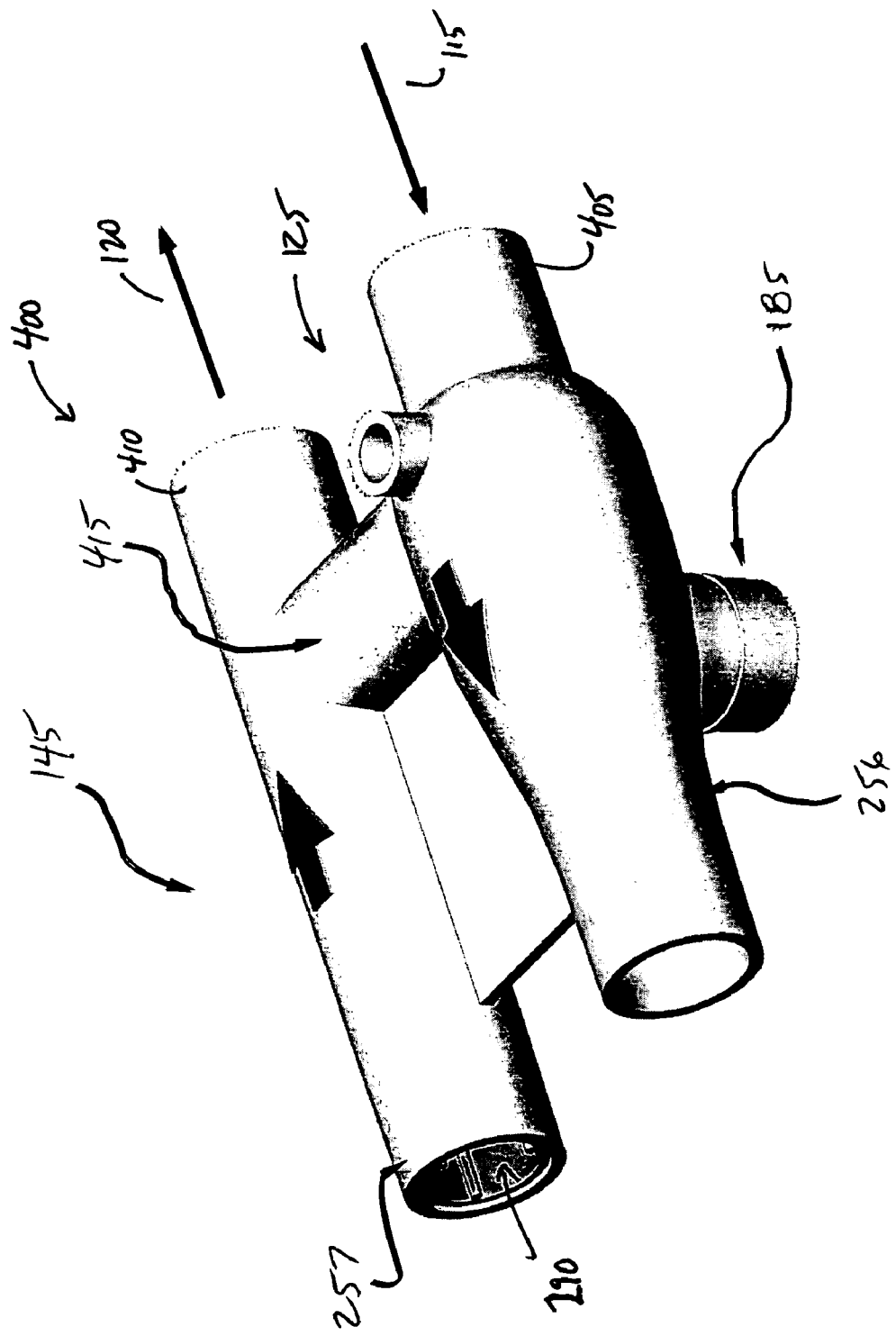

Another version of an aerosol introducer 145 that is integrated into a Y-piece junction 125 is shown in FIGS. 8A and 8B. The aerosol introducer 145 of FIGS. 8A and 8B comprises an H-shaped body 400. At a first end of the H-shaped body 400, a first connector 405 and a second connector 410 are adapted to be connectable to an inhalation line 115 and an exhalation line 120 of a ventilator circuit 110, respectively. Within the H-shaped body 400 and cross channel 415 provides a lumen so that air may flow from the first connector 405 to the second connector 410. As such, the connectors 405, 410 and the cross channel 415 serve as the junction 125 of the inhalation line 115 and the exhalation line 120 in a manner similar to that of a conventional Y-piece. The wall 255 in this version is in the form of two tubes 256, 257 that define the first channel 265 and second channel 260, respectively. As best shown in the exploded view of FIG. 8B, within the first channel 265 and at a position downstream (relative to the inhalation direction) of the cross channel 415, a one-way valve 270, as discussed above, is provided. In this version, the one-way valve 270 comprises a valve frame 271 that supports a flexible member 272. Within the second channel 260 and at a position upstream (relative to the exhalation direction) of the cross channel 415, a one-way valve 290, as discussed above, is provided.

Figure 8C:
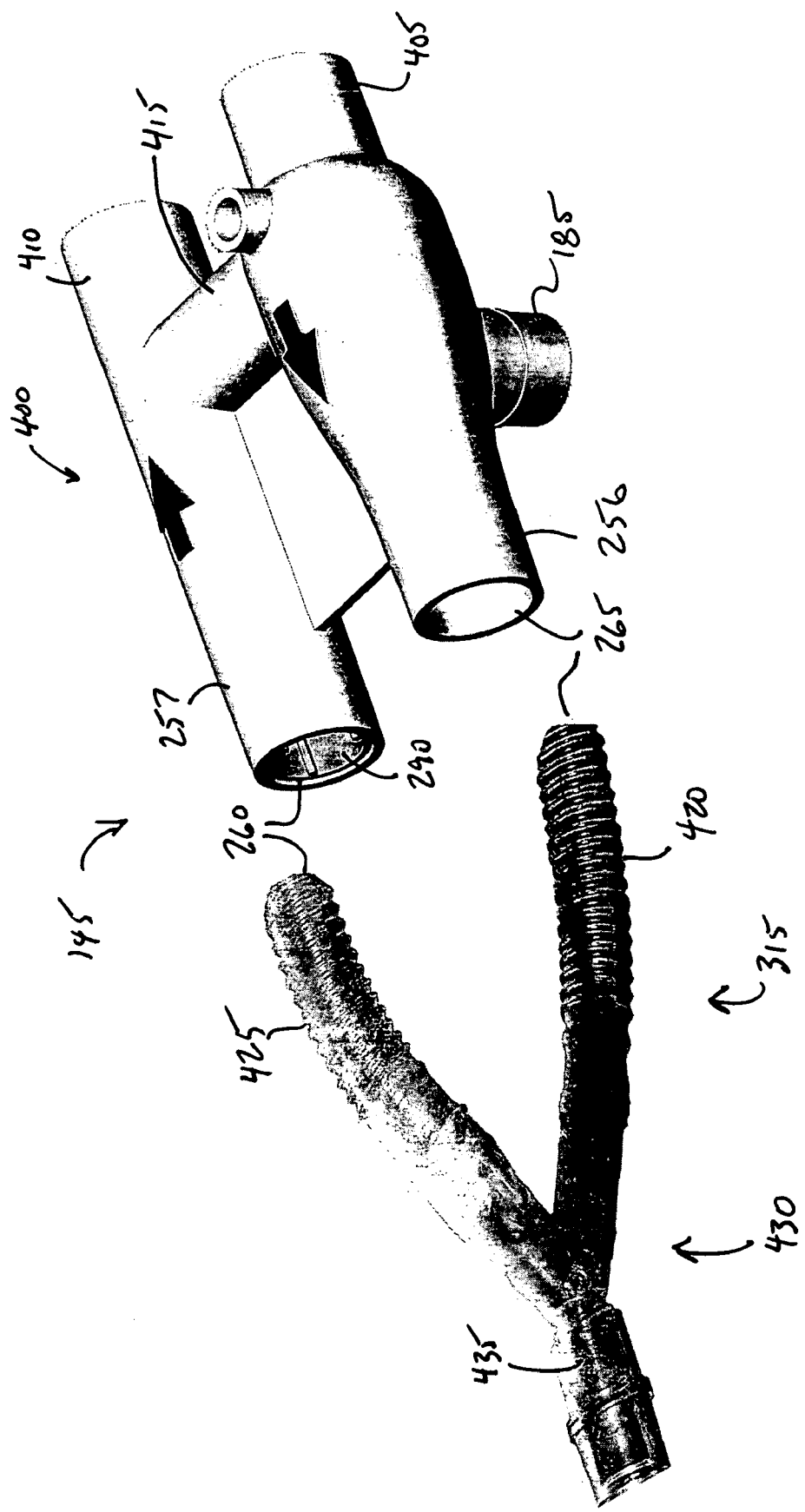

Optionally, as shown in FIG. 8C, a flexible portion 315 may be provided to facilitate the positioning of the aerosol introducer 145 in the ventilator circuit without interfering with the patient. In this version, the flexible portion 315 comprises a first flexible tube 420 that is connectable with the tube 256 forming the first channel 265, thereby extending the volume of the first channel 265. The flexible portion 315 in this version also comprises a second flexible tube 425 connectable with the tube 257 forming the second channel 260. The flexible tubes 420, 425 meet at a Y-connector 430 that is connectable at connection 435 to an endotracheal tube, either directly or indirectly.

The aerosolization apparatus 150 may be of any type that is capable of producing respirable particles or droplets. For example, the pharmaceutical formulation may be in a dry powder form, as described for example in PCT publication WO 99/16419; in U.S. Pat. No. 6,051,256, or in U.S. Pat. No. 6,503,483, all of which are incorporated herein by reference in their entireties. In such cases, the aerosolization apparatus 150 may comprise an active dry powder aerosolization apparatus, such as a aerosolization apparatus described in U.S. Pat. Nos. 5,485,135, 5,740,794, 6,257,233, all of which are incorporated herein by reference in their entireties, or a passive dry powder aerosolization apparatus, such as an aerosolization apparatus described in U.S. Pat. Nos. 4,069,819 and in 4,995,385, both of which are incorporated herein by reference in their entireties. Alternatively, the pharmaceutical formulation may comprise dissolved in or suspended in a liquid propellant, as described in U.S. Pat. Nos. 5,225,183; 5,681,545; 5,683,677; 5,474,759; 5,508,023; 6,309,623 and in U.S. Pat. No. 5,655,520 all of which are incorporated herein by reference in their entireties. In such cases, the aerosolization apparatus 150 may comprise a conventional metered dose inhaler (MDI). Alternatively, the pharmaceutical formulation may be in a liquid form and may be aerosolized using a conventional nebulizer as described in the aforementioned Gerald Smaldone et al's PCT patent application; in Gerald Smaldone et al's U.S. patent application Ser. No. 10/430,765, filed on May 6, 2003; in Gerald Smaldone et al's U.S. patent application Ser. No. 10/430,658, filed on May 6, 2003; and in U.S. Provisional Patent Applications 60/378,475; 60/380,783; 60/420,429; 60/439,894; and 60/442,785, all of which are incorporated herein by reference in their entireties. Other examples of suitable nebulizers include the Aeroneb® Go or Aeroneb® Pro, available from Aerogen, Inc. in Mountain View, Calif.; the PARI eFlow and other PARI nebulizers available from PARI Respiratory Equipment, Inc. in Midlothian, Va. 23112; the Lumiscope® Nebulizer 6600 or 6610 available from the Lumiscope Company, Inc. in East Brunswick, N.J.; and the Omron NE-U22 available from Omron Healthcare, Inc. in Kyoto, Japan.

It has been found that a nebulizer that forms droplets without the use of compressed gas, such as the Aeroneb Pro and the PARI eFlow, provides unexpected improvement in dosing efficiency and consistency. By generating fine droplets by using a vibrating perforated or unperforated membrane, rather than by introducing compressed air, the aerosolized pharmaceutical formulation can be introduced into the ventilator circuit 110 without substantially affecting the flow characteristics within the circuit and without requiring a substantial re-selection of the ventilator settings. In addition, the generated droplets when using a nebulizer of this type are introduced at a low velocity, thereby decreasing the likelihood of the droplets being driven to an undesired region of the ventilator circuit 110. Furthermore, the combination of a droplet forming nebulizer and an aerosol introducer 145 as described is beneficial in that there is a reduction in the variability of dosing when different tidal volumes are used by the ventilator, thus making the system more universal.

The volume of the first channel 265, that is the volume of the portion of the aerosol introducer 145 that receives the aerosolized pharmaceutical formulation and through which inhalation air flows, may be selected so that the aerosol delivery efficiency is increased for a particular ventilator and/or aerosolizer. For example, in the version of FIGS. 8A through 8C, the volume of the first channel 265, which includes the volume extending from the one-way valve 270 to the junction with the second channel 260 within the Y-piece 430, may be from about 10 ml to about 1000 ml. When the aerosol introducer 145 is being used in conjunction with a jet nebulizer, it may be desirable to have a larger first channel volume. Jet nebulizers introduce compressed air into the ventilator circuit, and the larger first channel volume reduces the impact of this introduction. Accordingly, it has been found that for jet nebulizer use, the first channel volume may be from about 50 ml to about 1000 ml, more preferably from about 100 ml to about 500 ml, more preferably from about 150 ml to about 250 ml, and most preferably about 200 ml. For vibrating mesh nebulizers, as the Aeroneb Pro and the PARI eFlow, reproducible administrations can result from smaller first channel volumes. It has been determined, for example, that the first channel volume for an aerosol introducer 145 used with a vibrating mesh nebulizer may be any volume greater than about 10 ml, more preferably from about 10 ml to about 1000 ml, more preferably from about 50 ml to about 200 ml, and most preferably about 90 ml.

Tables 1 and 2 summarize data generated to show the improved effectiveness of an aerosol introducer according to the present invention. In Table 1, the ventilator settings were selected so that the delivery efficiency of the aerosolize pharmaceutical formulation is optimized. In this version, humidity was turned off; bias flow was turned off, and the administration of aerosol was breath actuated. A control test was first run where aerosol from an Aerotech II+ jet nebulizer available from Aerogen is administered directly into the inhalation line 115 of a ventilator circuit in a conventional manner. In a second test, an aerosol introducer 145 of the type shown in FIGS. 8A-8C with a first channel volume of 150 ml was used to introduce aerosol generated from the Aerotech II+. In a third test, an aerosol introducer 145 of the type shown in FIGS. 8A-8C was used to introduce aerosol generated from an Aeroneb Pro vibrating mesh nebulizer and with a first channel volume of 90 ml. In Table 2, the ventilator setting were selected that are less favorable for aerosol delivery, but still within normal ventilator operating conditions. The same three tests were performed. As can be seen from viewing the data from Tables 1 and 2, the introduction of the aerosol using an aerosol introducer 145 of the present invention provides improved inhaled dose efficiency for both favorable and unfavorable ventilator settings. Accordingly, the aerosol introducer not only provides improved drug delivery, it allows for less stringent ventilator setting requirements.

TABLE 1

| TEST | Humidity | Bias Flow | Continuous Nebulization or Breath Actuation | Inhaled Dose (%) |
|---|---|---|---|---|
| 1 (Control) | Off | Off | Breath Actuated | 22 |
| 2 (Jet) | Off | Off | Breath Actuated | 25 |
| 3 (Vibrating) | Off | Off | Breath Actuated | 35 |

TABLE 2

| TEST | Humidity | Bias Flow | Continuous Nebulization or Breath Actuation | Inhaled Dose (%) |
|---|---|---|---|---|
| 1 (Control) | On | On | continuous | 9 |
| 2 (Jet) | On | On | continuous | 16 |
| 3 (Vibrating) | On | On | continuous | 38 |

Figure 9:
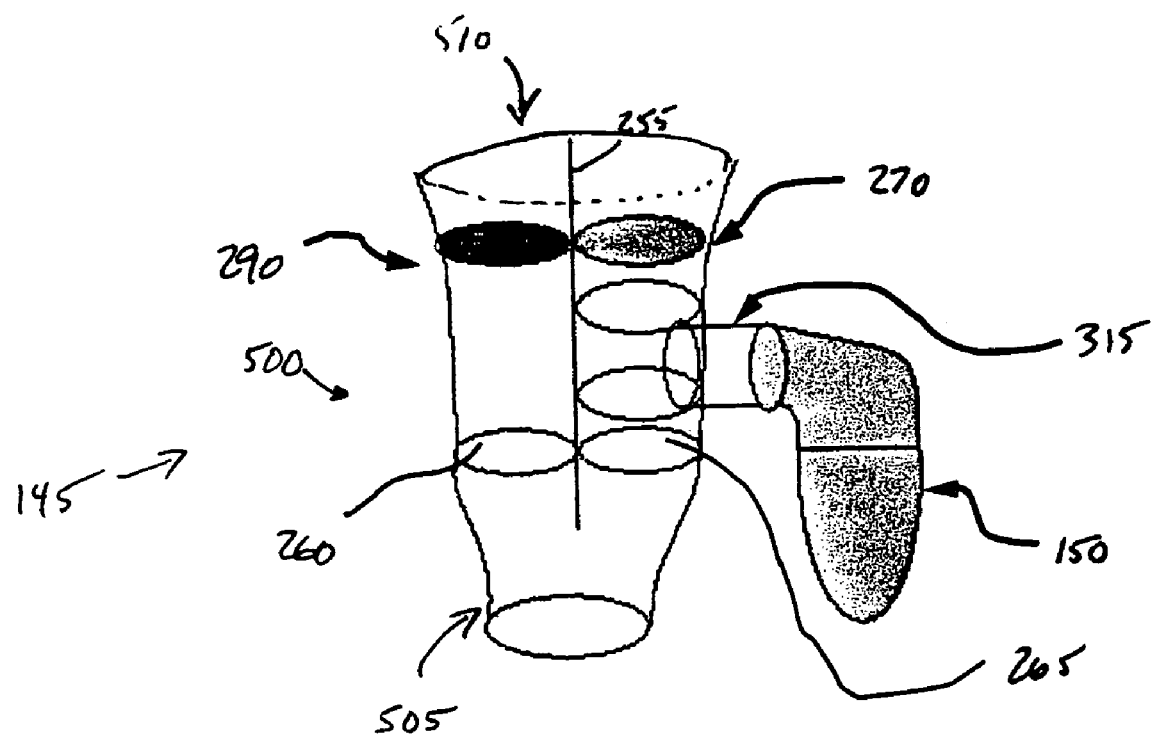
FIG. 9 is a schematic sectional side view of an aerosol introducer being used as a nebulizer mouthpiece.

In another version, as shown in FIG. 9, the aerosol introducer 145 may be used to administer aerosolized pharmaceutical formulation to patients other than those on a ventilator. For example, the aerosol introducer 145 may be used as a mouthpiece 500 for a nebulizer. Accordingly, the aerosol introducer 145 may have one end 505 that is shaped to be received in a user's mouth or nose, and the aerosol introducer may have a second end 510 that is open to ambient air. Any of the above mentioned versions may be modified in this manner.

The pharmaceutical formulation may comprise an active agent for administration to the respiratory tract of the user. The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system.

In one particular embodiment, the pharmaceutical formulation comprises an antibiotic for administration to a ventilated patient to treat or prevent ventricular assisted pneumonia. Such administration is described in aforementioned Gerald Smaldone et al's PCT patent application entitled "Methods, Devices and Formulations for Targeted Endobronchial Therapy"; in Gerald Smaldone et al's U.S. patent application Ser. No. 10/430,765, filed on May 6, 2003; in Gerald Smaldone et al's U.S. patent application Ser. No. 10/430,658, filed on May 6, 2003; and in U.S. Provisional Patent Applications 60/378,475; 60/380,783; 60/420,429; 60/439,894; and 60/442,785, all of which are incorporated herein by reference in their entireties. Using an aerosol introducer 145 according to the present invention in connection with the administration of aerosolized antibiotics offers substantial benefits. For example, when using the aerosol introducer 145 of the invention, substantially less pharmaceutical formulation is lost to the environment which results in a reduction in bacterial resistance against the antibiotic. In addition, the aerosol introducer 145 is able to deliver a more consistent dose which is particularly useful for antibiotic therapy. In one particular version, the pharmaceutical formulation may comprise vancomycin and/or gentamycin.

Alternatively or additionally, suitable active agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFIR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperatures (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), both of which are incorporated herein by reference in their entireties.

For MDI applications, the pharmaceutical formulation may also be treated so that it has high stability. Several attempts have dealt with improving suspension stability by increasing the solubility of surface-active agents in the HFA propellants. To this end U.S. Pat. No. 5,118,494, WO 91/11173 and WO 92/00107 disclose the use of HFA soluble fluorinated surfactants to improve suspension stability. Mixtures of HFA propellants with other perfluorinated cosolvents have also been disclosed as in WO 91/04011. Other attempts at stabilization involved the inclusion of nonfluorinated surfactants. In this respect, U.S. Pat. No. 5,492,688 discloses that some hydrophilic surfactants (with a hydrophilic/lipophilic balance greater than or equal to 9.6) have sufficient solubility in HFAs to stabilize medicament suspensions. Increases in the solubility of conventional nonfluorinated MDI surfactants (e.g. oleic acid, lecithin) can also reportedly be achieved with the use of co-solvents such as alcohols, as set forth in U.S. Pat. Nos. 5,683,677 and 5,605,674, as well as in WO 95/17195. Unfortunately, as with the prior art cosolvent systems previously discussed, merely increasing the repulsion between particles has not proved to be a very effective stabilizing mechanism in nonaqueous dispersions, such as MDI preparations. All of the aforementioned references being incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered or liquid formulation for use in the present invention includes an aerosol having a particle or droplet size selected to permit penetration into the alveoli of the lungs, that is, preferably 10 µm mass median diameter (MMD), preferably less than 7.5 µm, and most preferably less than 5 µm, and usually being in the range of 0.1 µm to 5 µm in diameter. When in a dry powder form, the pharmaceutical formulation may have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the relative positions of the elements in the aerosolization device may be changed, and flexible parts may be replaced by more rigid parts that are hinged, or otherwise movable, to mimic the action of the flexible part. In addition, the passageways need not necessarily be substantially linear, as shown in the drawings, but may be curved or angled, for example. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. An aerosol introducer for introducing an aerosolized pharmaceutical formulation into a ventilator circuit, the ventilator circuit comprising an endotracheal tube, an inhalation line extending from a ventilator for delivering inhalation flow from the ventilator, and an exhalation line extending from the ventilator for delivering exhalation flow to the ventilator, the aerosol introducer comprising:

a body comprising
   a first channel,
   a second channel,
   a cross channel,
   first and second connectors on one side of the body, the first connector being directly connectable to the inhalation line and the second connector being directly connectable to the exhalation line, and
   first and second inlets on a side of the body opposite to the side with the first and second connectors, the first and second inlets being connectable to a Y-piece, wherein the first channel extends from the first connector to the first inlet, wherein the second channel extends from the second connector to the second inlet, wherein the cross channel connects the first channel to the second channel at a position between the side with the connectors and the side with the inlets, and wherein the first connector and the second connector are separate connectors, a nebulizer inlet coupled to the body, the nebulizer inlet being adapted to receive an aerosolized pharmaceutical formulation, and a valving mechanism within the body comprising one or more valves, wherein at least one valve is a one-way valve such that, in use with the ventilation circuit, only inhalation flow may pass through the first channel.

2. An aerosol introducer according to claim 1 wherein the valving mechanism is adapted to reduce the loss of aerosolized pharmaceutical formulation to the exhalation line.

3. An aerosol introducer according to claim 1 wherein the valving mechanism comprises a one-way valve positioned within the first channel.

4. An aerosol introducer according to claim 3 wherein the valving mechanism comprises a one-way valve positioned within the second channel.

5. An aerosol introducer according to claim 1 wherein the valving mechanism comprises a one-way valve positioned within the second channel.

6. An aerosol introducer according to claim 1 in combination with the Y-piece, wherein the Y-piece is connectable to the endotracheal tube.

7. An aerosol introducer according to claim 1 further comprising a nebulizer associated with the nebulizer inlet.

8. An aerosol introducer according to claim 7 wherein the nebulizer comprises a vibrating mesh.

9. An aerosol introducer according to claim 1 wherein the nebulizer contains the pharmaceutical formulation and wherein the pharmaceutical formulation comprises amikacin.

10. An aerosol introducer according to claim 1 wherein the nebulizer contains the pharmaceutical formulation and wherein the pharmaceutical formulation comprises vancomycin.

11. An aerosol introducer according to claim 1 wherein the nebulizer contains the pharmaceutical formulation and wherein the pharmaceutical formulation comprises gentamycin.

12. An aerosol introducer according to claim 1 wherein the nebulizer contains the pharmaceutical formulation and wherein the pharmaceutical formulation comprises a fluoroquinolone.

13. An aerosol introducer according to claim 1 wherein the volume of the first channel is from about 10 mL to about 1000 mL.

* * * * *